United States Patent [19]

Yoshioka et al.

[11] Patent Number: 4,869,747
[45] Date of Patent: Sep. 26, 1989

[54] METHOD FOR GROWTH ACCELERATION OF PLANTS

[75] Inventors: Hiroshi Yoshioka, Gunma; Akira Yamamoto, Niigata; Minoru Takamizawa, Niigata; Toshinobu Ishihara, Niigata, all of Japan

[73] Assignee: Shin-Etsu Chemical Co., Ltd., Tokyo, Japan

[21] Appl. No.: 651,599

[22] Filed: Sep. 17, 1984

[30] Foreign Application Priority Data

Sep. 17, 1983 [JP] Japan .................................. 58-171497

[51] Int. Cl.$^4$ ...................... A01N 37/00; A01N 37/16; C07F 7/02; C07F 7/04
[52] U.S. Cl. .......................................... 71/106; 71/79; 71/97; 71/113; 71/77; 556/438; 528/26
[58] Field of Search ...................... 71/79, 106, 113, 97; 556/438; 528/26

[56] References Cited

U.S. PATENT DOCUMENTS

| | | | |
|---|---|---|---|
| 2,416,198 | 2/1947 | Moyer | 71/113 |
| 2,535,875 | 12/1950 | Stewart | 71/97 |
| 2,842,517 | 7/1958 | Schorr | 528/26 |
| 3,898,257 | 8/1975 | Gregory | 71/79 |
| 3,985,780 | 10/1976 | Foery et al. | 71/79 |

FOREIGN PATENT DOCUMENTS 0151975 11/1979 Japan ...................................... 71/97

OTHER PUBLICATIONS

Oikawa et al., "Carboxyethylgermanium sesquioxide as plant growing improvers", Chem. Abs. 76:109220s (1972).

Primary Examiner—Glennon H. Hollrah
Assistant Examiner—Konstas
Attorney, Agent, or Firm—Jules E. Goldberg

[57] ABSTRACT

A novel method for accelerating growth of a plant in agriculture and forestry is proposed in which an organosilicon compound ω-carboxyalkylsilicon sesquioxide, e.g. 2-carboxyethylsilicon sesquioxide, of the unit formula $$HOOC(CH_2)_n SiO_{1.5},$$

in which n is a positive integer of 1 to 4, is applied to the plant directly or to the soil in which the plant is growing. The metal salts or complexes of the above compound as well as the precursor compounds thereof readily convertible to the silsesquioxide compound by hydrolysis are also effective.

4 Claims, No Drawings

METHOD FOR GROWTH ACCELERATION OF PLANTS

BACKGROUND OF THE INVENTION

The present invention relates to a method for accelerating growth of a plant or, in particular, accelerating growth of a plant by the application of a specific organosilicon compound thereto.

As is known, there is a great demand for a growth controlling or accelerating agent for plants in agriculture and forestry and conventionally used growth accelerating agents include auxins such as indoleacetic acid and naphthylacetic acid, gibberellins, triacontanols and the like. These growth accelerating agents for plants are indeed not ineffective but have their respective disadvantages such as insufficient effectiveness for growth acceleration, applicability to limited species of plants or to limited purposes, expensiveness to prohibit the use thereof in the practical application and in other respects.

Accordingly, it has been eagerly desired to develop an improved method for accelerating growth of plants by use of a growth accelerating agent free from the above mentioned disadvantages in the prior art growth accelerating agents for plants.

SUMMARY OF THE INVENTION

It is therefore an object of the present invention to provide a novel and improved method for growth acceleration of a plant without the problems and disadvantages accompanying the use of conventional growth accelerating agents. That is, the method of the invention is performed by use of a growth accelerating agent which is very versatile in its applicability and effectiveness and has good availability with inexpensiveness.

Thus, the method of the present invention for accelerating growth of a plant comprises applying an organosilicon compound selected from the class consisting of $\omega$-carboxyalkyl silane compounds represented by the general formula

in which R is a hydrogen atom or an alkyl group, X is a hydrolyzable atom, e.g. halogen, or hydrolyzable group, e.g. alkoxy group, and n is a positive integer of 1, 2, 3 or 4, $\omega$-carboxyallkylsilicon sesquioxides as a hydrolysis-condensation product of the above mentioned silane compound represented by the unit formula

in which n has the same meaning as defined above, and metal salts and complexes thereof, preferably, in the form of an aqueous solution to the plant directly or to the soil in which the plant is growing.

DETAILED DESCRIPTION OF THE PREFERRED EMBODIMENTS

The above mentioned silane compound of the formula (I) is a well known organosilicon compound and the application of this compound as such to the plant or to the soil is of course effective for growth acceleration of plants. It is presumable that this silane compound is readily hydrolyzed and at least partially condensed by dehydration into the silsesquioxide compound of th formula (II) when the silane compound such as an $\omega$-carboxylalkyl trialkoxysilane is contacted with water after application. In this sense, the effective ingredient for growth acceleration of plants may not be the silane comound per se but rather the silsesquioxide compound. Accordingly, it is preferable to use the silsequioxide compound rather than the silane compound due to the stability of the former against hydrolysis during storage and use in the fields. Such a silsesquioxide compound of the formula (II) can readily be prepared by the hydrolysis and partial condensation of the hydrolyzate of the silane compound.

The $\omega$-carboxyalkylsilicon sesquioxide of the formula (II) is obtained usually in the form of a white powder which is readily dissolved in warm or hot water to give an aqueous solution of any desired concentration. The suffix n in the formula (II) is an integer of 1 to 4 but preferably 2 so that the compound is 2-carboxyethylsilicon sesquioxide. This compound can be prepared by the hydrolysis of 2-cyanoethyl trichlorosilane followed by the reaction of the hydrolyzate with an alkali hydroxide and neutralization of the reaction mixture with acetic acid to precipitate the desired product.

In addition to the above described silsesquioxide compound in the free acid form, similar effectiveness is noted for metal salts and complexes of the silsesquioxide compound which is obtained also in a powdery form. The metallic element to form the salt or complex of the silsesquioxide compound is not particularly limitative provided that the salt or complex has a solubility in water to ensure preparation of an aqueous solution of a desired concentration. Preferable metallic elements include, for example, calcium, iron, manganese and molybdenum though not limited thereto.

The manner of application of theorganosilicon compound is not particularly limitative and the silsesquioxide compound in the powdery form can be sprinkled as such on the plant or on the soil in which the plant is growing followed by sprinkling of water or spread on the soil as blended with fertilizers. It is, however, preferable that the silsesquioxide compound is dissolved in advance in water to give an aqueous solution of a desired concentration and the aqueous solution is sprinkled or sprayed onto the plant or soil by use of a conventional sprinkling or spraying machine. The optimum concentration of the aqueous solution of course widely differs from plant to plant or from stage to stage of the plant growing but the concentration should usually be in the range from 10 to 10,000 ppm by weight.

The silsesquioxide compounds proposed in the present invention have effectiveness for growth acceleration of a wide variety of plants including not only the agricultural and horticultural plants grown in the fields such as cereals, e.g. rice, wheat, barley and indian corn, and vegetables, e.g. cucumber, eggplant, tomato, potato, onion and lettuce, as well as various flowers but also seedlings and young trees by cuttages in gardening and forestry for buildings and pulp industry under no limitations by the geographical conditions. It is further important that the growth accelerating agent used in the inventive method is physiologically inert to human body so that the method is free from the problem of safety by the remaining chemicals even when the method is applied to edible plants for foods.

In the following, the inventive method and effectiveness thereof are described in more detail by way of examples.

Preparation of 2-carboxyethylsilicon sesquioxide

A mixture of 50 g of 2-cyanoethyl trichlorosilane of 97% purity and 100 ml of cold water was admixed with 80 g of a 30% by weight aqueous solution of sodium hydroxide to effect complete hydrolysis of the silane compound. Neutralization of the aqueous solution taken by separating from the above reaction mixture caused precipitation of white crystals which were collected by filtration, washed with 100 ml of cold water and dried under reduced pressure to give 30 g of 2-carboxyethylsilicon sesquioxide.

Substantially the same procedure as above could be applied to the preparation of carboxymethylsilicon, 3-carboxypropylsilicon and 4-carboxybutylsilicon sewquioxides.

EXAMPLE 1

Each of the carboxymethylsilicon, 2-carboxyethylsilicon, 3-carboxypropylsilicon and 4-carboxybutylsilicon sesquioxides was dissolved in warm water in a concentration of 1000 ppm by weight.

Each a 1.5 g portion of cellulose powder was packed to the bottom of glass tubes of 27 mm inner diameter and 118 mm depth and the powder was wetted with 6 ml of one of the above prepared 4 aqueous solutions or with pure water. Two glass tubes were prepared in this manner for each of the solutions and pure water. Six seeds of a paddy-rice plant at incipient germination each with a 1 mm bud grown under the same conditions were placed on the surface of the wet cellulose powder in each of the above prepared 10 glass tubes and kept at 30° C. under a luminosity of 300 lux for 10 days. The effect of the silsesquioxide compounds on the growth rate of the rice seedlings was examined by measuring the length of the second leaf sheaths after 10 days growing under the above described conditions to give the results shown in Table 1 below with the averaged values for 12 seedlings grown with each of the solutions or pure water.

TABLE 1

| -Carboxyalkylsilicon sesquioxide | Length of second leaf sheath, cm | Increase over the control, % |
| --- | --- | --- |
| None (control) | 11.7 | — |
| Carboxymethylsilicon sesquioxide | 12.8 | 9.4 |
| 2-Carboxyethylsilicon sesquioxide | 15.9 | 35.9 |
| 3-Carboxypropylsilicon sesquioxide | 14.4 | 23.4 |
| 4-Carboxybutylsilicon sesquioxide | 12.9 | 10.3 |

The above given results clearly indicate that the silsesquioxide compounds tested are all effective in accelerating the growth of rice seedlings. In particular, 2-carboxyethylsilicon sesquioxide is the most effective.

EXAMPLE 2

The same experimental procedure as above was repeated except that 2-carboxyethylsilicon sesquioxide alone was used as the silsesquioxide compound and the concentration of the compound in the aqueous solution was varied as 0.1 ppm, 1 ppm, 10 ppm, 100 ppm, 1,000 ppm and 10,000 ppm. The results are shown in Table 2 below, in which the data for the control and the 1000 ppm solution are the same as in Table 1 above.

TABLE 2

| Concentration of silsesquioxide, ppm | Length of second leaf sheath, cm | Increase over the control, % |
| --- | --- | --- |
| 0 (control) | 11.7 | — |
| 0.1 | 11.8 | 0.9 |
| 1 | 12.5 | 6.8 |
| 10 | 12.9 | 10.3 |
| 100 | 13.8 | 17.9 |
| 1,000 | 15.9 | 35.9 |
| 10,000 | 14.1 | 20.5 |

As is understood from the above results, remarkable effect is obtained from the growth acceleration of rice seedlings with 2-carboxyethylsilicon sesquioxide when the concentration thereof in the aqueous solution is 100 to 10,000 ppm.

EXAMPLE 3

Substantially the same experimental procedure was repeated as in Example 1 except that the silsesquioxide compound was replaced with the same amount of calcium or iron salt of 3-carboxypropylsilicon sesquioxide. The results were as shown in Table 3 below, in which the data for the control are the same as in Table 1. As is understood from these results, about the same effect is obtained with the metal salts as with the silsesquioxide compound in the acid form.

TABLE 3

| Metallic element in the salt of silsesquioxide | Length of second leaf sheath, cm | Increase over the control, % |
| --- | --- | --- |
| No silsesquioxide (control) | 11.7 | — |
| Calcium | 14.8 | 26.5 |
| Iron | 13.8 | 17.9 |

EXAMPLE 4

A 1% by weight aqueous solution of 2-carboxyethylsilicon sesquioxide was given to a group of young juniper trees (*Juniperus virginiana*) of 2 years old grown in nursery by cuttage and having an average height of 48 cm by pouring the solution onto the soil around the root in a volume of 100 ml per tree in every month from April to October. The average height of these trees after 1 year measured in April of the next year was 97 cm.

For comparison, another group of young trees of the same species prepared in the same manner as in the above tested young trees were grown under the same conditions as above excepting the omission of watering with the aqueous solution of the silsesquioxide compound. The average height of these control trees after 1 year was 75 cm indicating a 63% increase of growth over the control obtained by the application of the silsesquioxide compound.

What is claimed is:

1. A method for accelerating growth of a plant which comprises applying a growth accelerating effective amount of an organosilicon compound selected from the class consisting of ω-carboxyalkyl silane compounds represented by the general formula $$ROOC(CH_2)_nSiX_3,$$

in which R is a hydrogen atom or an alkyl group, X is a hydrolyzable atom or group and n is a positive integer of 1, 2, 3 or 4, ω-carboxyalkylsilicon sesquioxides represented by the unit formula $$HOOC(CH_2)_nSiO_{1.5},$$

in which n has the same meaning as defined above, and metal salts and complexes thereof to the plant directly or to the soil in which the plant is growing.

2. The method as claimed in claim 1 wherein the organosilicon compound is the ω-carboxyalkylsilicon sesquioxide.

3. The method as claimed in claim 2 wherein the ω-carboxyalkylsilicon sesquioxide is 2-carboxyethylsilicon sesquioxide.

4. The method as claimed in claim 2 wherein the ω-carboxyalkylsilicon sesquioxide is applied in the form of an aqueous solution.

* * * * *